United States Patent
Emken et al.

(10) Patent No.: US 10,254,566 B2
(45) Date of Patent: Apr. 9, 2019

(54) ALIGNMENT FEATURES THAT ALLOW FOR A LIQUID FILLED LAYERED STACK TO ASSEMBLE

(71) Applicant: Verily Life Sciences LLC, Mountain View, CA (US)

(72) Inventors: Jeremy L. Emken, San Jose, CA (US); Scott B. Kennedy, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 366 days.

(21) Appl. No.: 15/278,394

(22) Filed: Sep. 28, 2016

(65) Prior Publication Data
US 2018/0088354 A1 Mar. 29, 2018

(51) Int. Cl.
| | |
|---|---|
| G02C 7/08 | (2006.01) |
| G02C 7/04 | (2006.01) |
| G02C 7/02 | (2006.01) |
| A61F 2/16 | (2006.01) |
| G02B 7/00 | (2006.01) |

(52) U.S. Cl.
CPC .......... *G02C 7/083* (2013.01); *A61F 2/1605* (2015.04); *A61F 2/1613* (2013.01); *A61F 2/1627* (2013.01); *G02B 7/003* (2013.01); *G02C 7/021* (2013.01); *G02C 7/04* (2013.01);
(Continued)

(58) Field of Classification Search
None
See application file for complete search history.

(56) References Cited

U.S. PATENT DOCUMENTS

| | | | |
|---|---|---|---|
| 5,219,497 | A | 6/1993 | Blum |
| 6,319,433 | B1 | 11/2001 | Kohan |

(Continued)

FOREIGN PATENT DOCUMENTS

| | | |
|---|---|---|
| JP | 2011-158634 A | 8/2011 |
| WO | 2009/126946 A1 | 10/2009 |
| WO | 2013/176768 A1 | 11/2013 |

OTHER PUBLICATIONS

PCT/US2017/053549—International Search Report and Written Opinion of the International Searching Authority, dated Jan. 5, 2018, 18 pages.

*Primary Examiner* — Edward Glick
*Assistant Examiner* — Anthony G Quash
(74) *Attorney, Agent, or Firm* — Christensen O'Connor; Johnson Kindness PLLC

(57) ABSTRACT

Apparatus and systems for an ophthalmic device having alignment features for a liquid filled layered stack to assemble are disclosed herein. An example apparatus may include first, second, and third optical elements arranged in a stack, with each optical element including alignment and separation features. The alignment and separation features may form a reservoir region and a dam region. The reservoir region may provide radial alignment to the first, second, and third optical elements such that an optical axis of each optical element is aligned, and the reservoir region may have a reservoir region gap formed between adjacent ones of the optical elements. The dam region, disposed radially outside of the reservoir region, may include a first dam formed due to the first and second optical elements being in contact, and a second dam formed due to the second and third optical elements being in contact, wherein the dam region determines a reservoir region gap width.

25 Claims, 4 Drawing Sheets

(52) U.S. Cl.
CPC .............. *G02C 7/049* (2013.01); *G02C 7/041* (2013.01); *G02C 2202/16* (2013.01)

(56) References Cited

U.S. PATENT DOCUMENTS

| | | |
|---|---|---|
| 7,499,223 B2 | 3/2009 | Berge et al. |
| 2010/0265456 A1 | 10/2010 | Matsui |
| 2014/0192313 A1 | 7/2014 | Riall et al. |

ALIGNMENT FEATURES THAT ALLOW FOR A LIQUID FILLED LAYERED STACK TO ASSEMBLE

TECHNICAL FIELD

This disclosure relates generally to ophthalmic devices, and in particular but not exclusively, relates to alignment and separation features on optical elements of stacked lens structures.

BACKGROUND INFORMATION

Presbyopia may be treated with wearable or implantable lenses that provide accommodation. For example, a lens may provide accommodation through electrical stimulation of liquid crystal material included in the lens. The lenses, either implanted or worn on the surface of the eye similar to a contact lens, may include multiple layers of material to provide the accommodation and associated control.

The multiple layers, however, may complicate fabrication of the lens due to the size of the components that form the multiple layers and alignment requirements. For example, an optical axis of the lens may add an alignment constraint to the fabrication of the lens. Misalignment of the optical axis of the multiple layers may result in blurred vision. While many fabrication techniques may be available to provide the desired alignment, additional factors of the lens may not be addressed by such techniques.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and apparatus that include alignment and separation features on optical elements of stacked lens structures allowing for the assembly of the stacked lens structures are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
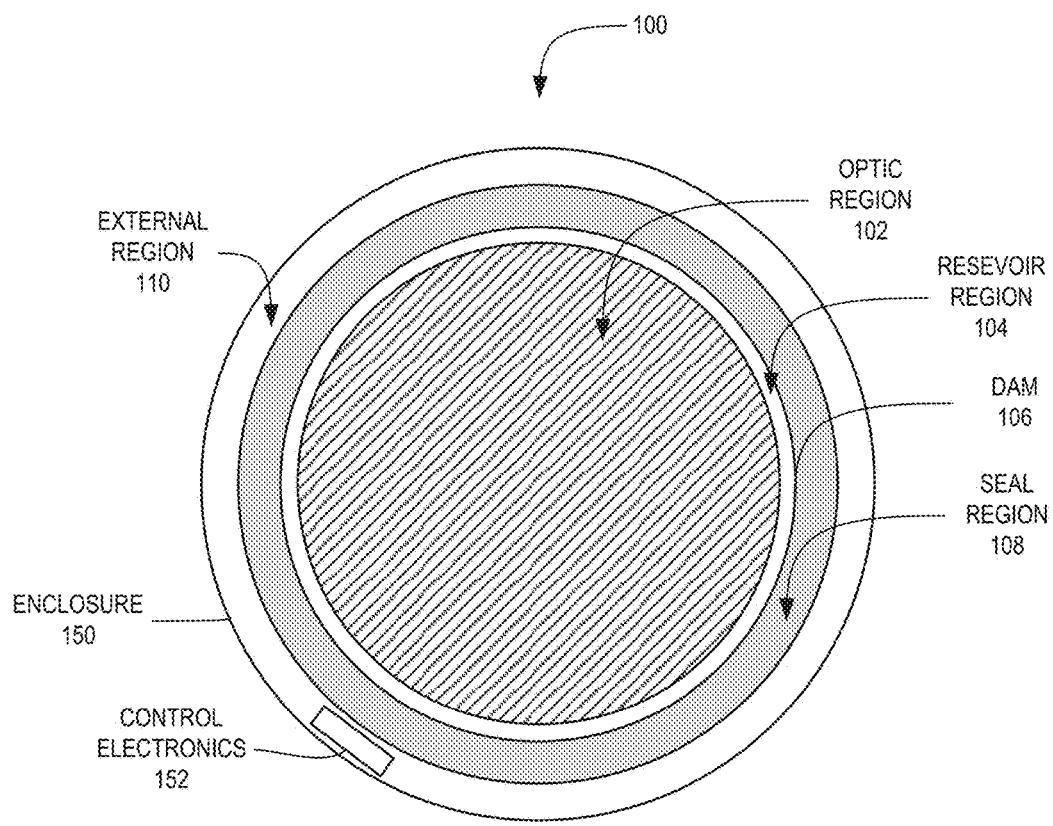
FIG. 1A is a plan view of an ophthalmic device including alignment and separation features in accordance with an embodiment of the disclosure.
Figure 1B:
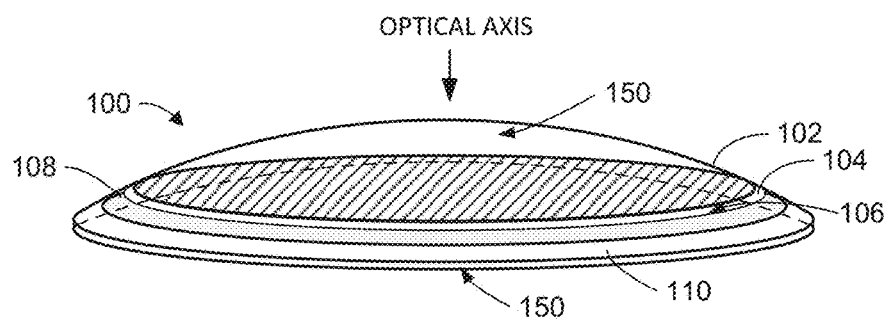
FIG. 1B is a perspective view of an ophthalmic device including alignment and separation features in accordance with an embodiment of the disclosure.

FIGS. 1A and 1B are a plan view and a perspective view, respectively, of an ophthalmic device 100 in accordance with an embodiment of the present disclosure. The ophthalmic device 100 may be an on-eye wearable device, such as a contact lens, or an implantable device, such as an intraocular lens (IOL). In some embodiments, the ophthalmic device 100 may be implemented as a smart contact lens that mounts over a user's eye or as an IOL that is implanted into the anterior chamber, the posterior chamber, or other locations of the user's eye. In either or both embodiments, the ophthalmic device 100 may include alignment and separation features that provide for radial alignment between multiple optical elements of the ophthalmic device 100 and further provide separation setting features that determine and set a gap of a desired width between adjacent ones of the multiple optical elements.

The ophthalmic device 100 may, in general, be disc-shaped, and may have an anterior side, e.g., an external facing side, and a posterior side, e.g., an eye-ward or corneal side. The ophthalmic device 100 may additionally be dome shaped such that the anterior side is convex and the posterior side is concave. In general, the ophthalmic device 100 may have a radius of curvature around a central axis that may be similar to a radius of curvature of at least a portion of a user's eye, such as the cornea. In some embodiments, the central axis may also be an optical axis of the ophthalmic device 100.

The illustrated embodiment of the ophthalmic device 100 includes a plurality of optical elements disposed in enclosure 150. In some embodiments, the plurality of optical elements may be formed into an optical stack having, for example, a posterior optical element, a middle optical element, and an anterior optical element. The plurality of optical elements and at least a portion of the enclosure 150 may be formed with the radius of curvature as discussed above. Each of the plurality of optical elements (discussed in more detail in FIGS. 2 and 3) may have the alignment and separation features formed therein and/or thereon. For example, the alignment and separation features may be grooves and/or ridges that form rings around the optical elements at one or more desired radii. For example, the one or more desired radii may be 4 to 10 mm from a central axis, which may coincide with an optical axis, of the ophthalmic device 100. In general, the radial location of the alignment and separation features may be influenced by various other aspects of the ophthalmic device 100, such as a desired area for an optic region, etc. The alignment and separation features may form or define various regions in the ophthalmic device 100, such as an optic region 102, a reservoir region 104, a dam 106, and a seal region 108. The ophthalmic device, in some embodiments, may further include an external region 110. The various regions may include gaps between adjacent optical elements that are formed by the alignment and separation features. Additionally, the alignment and separation features may assist with assembly of the ophthalmic device 100.

The enclosure 150 may be formed from a material amenable to being worn on a user's eye, or implantable into a user's eye, and may further be an optically transmissive material (e.g., transparent, clear, etc.) that seals the internal components and protects the eye. Enclosure 150 may have concave and convex surfaces similar to a contact lens, have generally flat surfaces, or otherwise in various embodiments. In a contact lens embodiment, enclosure 150 may be implemented as a hydrogel or other permeable polymer material that permits oxygen to reach the eye, or non-permeable materials (e.g., glass, plastic, silicon) may also be used. In an IOL embodiment, enclosure 150 may be implemented as a silicon enclosure, or other hermetically sealable materials. Of course, other optically transmissive and biocompatible materials may be used.

The optic region 102 may be an optically active area that provides adjustable optical power using a liquid crystal material, for example. The optic region 102 may encompass a central diameter and may include an optical axis of the ophthalmic device 100. In some embodiments, the optic region 102 may be around 5 mm in diameter and may be centered on the optical axis. The liquid crystal material may be disposed in gaps formed between adjacent ones of the plurality of optical elements. For example, transparent or semi-transparent electrodes (not shown) of the ophthalmic device 100 may be energized by one or more power sources controlled by control electronics 152 to change an orientation of the liquid crystals of the liquid crystal material with respect to one or more optical elements of the plurality of optical elements. The change in orientation of the liquid crystal material may cause a change in optical power of the ophthalmic device 100, which may provide accommodation to a user.

The reservoir region 104 may be radially outside of and adjacent to the optic region 102. Alignment and separation features of each of the plurality of optical elements may be arranged to form the reservoir region 104. The reservoir region 104 may be formed by gaps between adjacent ones of the optical elements, which may be smaller than, equal to, or greater than the gaps associated with the optic region 102. The reservoir region 104 may hold excess liquid crystal material outside of the optic region 102, which may be included in the ophthalmic device 100 during assembly, for example.

The dam 106 may prevent liquid crystal from escaping out of the reservoir region 104, and may prevent sealant material disposed in the seal region from breaching the reservoir region in a radially inward direction. The dam 106 may also determine gap widths between the optical elements in the optic region 102 and the reservoir region 104. The dam 106 may be formed by interlocking the alignment and separation features of the optical elements. For example, a sidewall, e.g., flat area, of a ridge formed in one optical element may contact, e.g., rest upon, a sidewall of a groove formed in an opposing optical element. Alternatively or additionally, the dam 106 may be formed by mating curves of similar or different radii of curvature, or mating, e.g., nesting, v-shaped features. In some embodiments, the alignment and separation features formed on each optical element may be slightly offset from associated features in the opposing elements so that the dam 106 is formed.

The seal region 108 may be formed radially outward of the dam 106. The seal region 108 may be formed by large gaps between adjacent ones of the optical elements and that may allow a sealant to be formed therein to seal in the liquid crystal material. Example sealants may include a gasket or a curable adhesive, to name a couple. The seal region 108 may be formed, for example, due to the alignment and separation features and further due to a thickness of the optical elements reducing in the seal region 108.

In some embodiments, the external region 110 may be radially outside of the seal region 108. The external region 110 may include edges of the optical elements, control circuitry substrates, such as control electronics 152, and where an anterior portion and a posterior portion of the enclosure 150 intersect and seal. In some embodiments, one or more substrates for supporting electrical components and connections to conductors may be included in the external region 110. For example, a disc-shaped substrate may be included outside of the seal region 108 that supports the control electronics 152 and connections.

The various regions of the ophthalmic device 100 may, in general, include gaps between adjacent ones of the plurality of optical elements that are formed by the associated alignment and separation features of the optical elements. The alignment and separation features, to be discussed in more detail below, may assist with setting widths of the gaps and that further assist with radial alignment of the optical elements to obtain concentricity between the optical elements.

Figure 2:
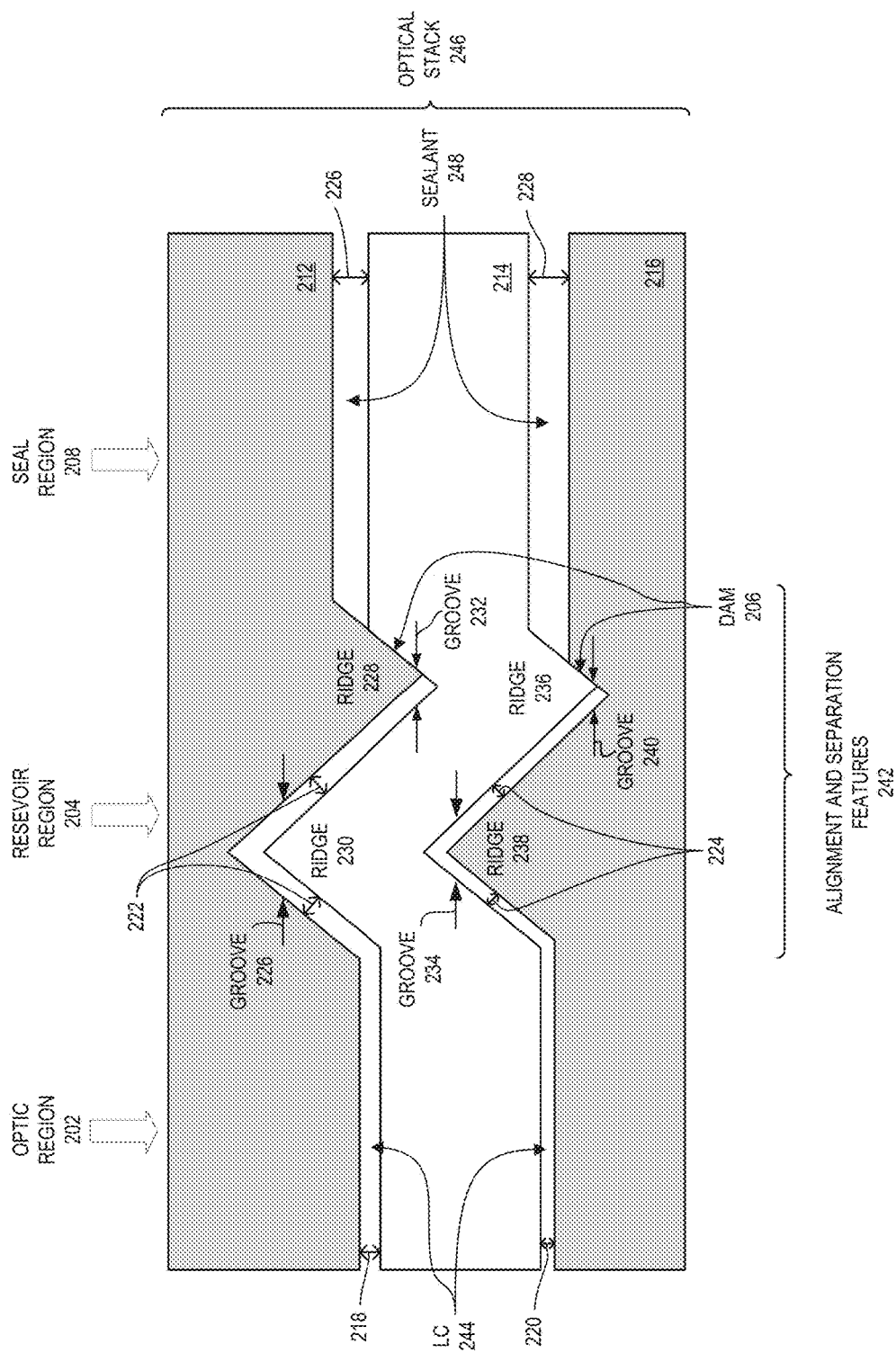
FIG. 2 is a cross-sectional view of an optical stack including alignment and separation features in accordance with an embodiment of the disclosure.

FIG. 2 is a cross-sectional view of an optical stack 246 including alignment and separation features in accordance with an embodiment of the present disclosure. The optical stack 246 may be an example of an optical stack included in the ophthalmic device 100. The illustrated embodiment of the optical stack 246 includes optical elements 212, 214, and 216 having alignment and separation features 242 formed in or on surfaces thereof. The alignment and separation features 242 may define an optic region 202, a reservoir region 204, a dam 206, and a seal region 208 of the optical stack 246. The various regions may relate to operational related aspects and/or assembly related aspects of the ophthalmic device 200.

In general, the combination of the optical elements 212-216 may form a lens that may either be worn on a user's eye or implanted into a user's eye. At least one of the optical elements 212-216 in conjunction with a liquid crystal material included in gaps between the optical elements 212-216 may provide a dynamic optic capable of providing accommodation to the user.

The optical stack 246 may be formed from the optical elements 212-216. Optical elements 212 and 216 may be on opposing sides of optical element 214, such that optical element 214 is sandwiched between optical elements 212 and 216. In some embodiments, optical element 212 may be on an anterior side of the ophthalmic device 200, while the optical element 216 may be on a posterior side. In such an embodiment, the optical element 212 may be external facing, whereas the optical element 216 may be eye-ward or corneal facing. While these designations may be adopted for use in discussion of the present disclosure, they are by no means limiting, and the opposite designations may be adopted instead. The optical stack 246 may be encased in an enclosure 150. In general, the optical stack 246 may provide the optically active elements of the ophthalmic device, at least within an optic region 202.

Optical element 212 may be a planar substrate formed into disc. In some embodiments, the planar substrate may be dome-shaped such that a convex side is posterior facing and a concave side faces the optical element 214. Optical element 212 may include one or more features around the disc-shaped planar substrate, which may be formed on the anterior side of the optical element 212. The one or more features may be disposed at a desired radius from a central axis of the optical element 212, and in some embodiments, the one or more features may extend from a first radius to a second radius. These features, such as the groove 226 and the ridge 228, may be physical features cut or molded into the material of the optical element 212. The groove 226 and the ridge 228 may be part of the alignment and separation features 242 that are associated with the optical element 212. While only a single groove and a single ridge are shown, the alignment and separation features may include multiple grooves and ridges. Optical element 212 may be formed from a polymer, and may be a rigid, gas permeable polymer in some embodiments. The optical element 212 may or may not have optical power, such as a static optical power.

Optical element 214 may be a planar substrate also formed into a disc. Similar to optical element 212, optical element 214 may be dome-shaped with a convex side facing optical element 212 and a concave side facing optical element 216. In the optic region 202, the optical element 214 may have a diffraction lens structure formed on one or both sides, which, in combination with liquid crystal material 244, may provide a dynamic optic. Additionally, optical element 214 may include one or more physical features at a desired radius, which may at least partially align with the radius the physical features of optical element 212 are located. In some embodiments, the one or more physical features may be formed on both surfaces of the planar substrate, e.g., a posterior surface and an anterior surface. For example, the one or more physical features may include a ride 230 and a groove 232 formed on a posterior side, and a groove 234 and a ridge 236 formed on an anterior side of the optical element 214. The grooves 232, 234 and ridges 230, 236 may combined form alignment and separation features 242 associated with the optical element 214. In some embodiments, the apex of the ridge 230 and the base of the groove 234 may align. The groove 232 and the ridge 236 may similarly align. These features of the optical element 214 may appear as a zig zag when viewed from the side, as shown in FIG. 2. The grooves and ridges 232, 234 and ridges 230, 236 may combined to form kinks or buckles in the optical element 214 that when viewed from above may appear as topographical rings around the optical element 214, which may be disposed at one or more desired radii from a central axis of the optical element 214. While optical element 214 is shown to include two ridges and two grooves, e.g. a posterior kink and an anterior kink, there may be multiple kinks in the optical element 214 to form associated alignment and separation features 242. Similar to the optical element 212, the grooves 232, 234 and ridges 230, 236 may be cut into or molded into a polymer material, such as a rigid, gas permeable polymer, used to form the optical element 214.

Optical element 216 may be a planar substrate formed into disc similar to the optical element 212. In some embodiments, the planar substrate may be dome-shaped such that a convex side faces optical element 214 and a concave side is eye-ward facing. Optical element 216 may include one or more features disposed at a desired radius of the disc-shaped planar substrate, which may be formed on the posterior side of the optical element 216. In some embodiments, the desired radius may at least partially align with the radius the one or more features of the optical element 214 on the posterior side are disposed. These features, such as the ridge 238 and the groove 240, may be physical features cut or molded into the material forming the optical element 216.

The groove 240 and the ridge 238 may be part of the alignment and separation features 242 that are associated with the optical element 216. While only a single a single instance of the alignment and separation features is shown, multiple instances of the alignment and separation features may be included in the optical stack 246. Optical element 216 may be formed from a polymer, and may be a rigid, gas permeable polymer in some embodiments. The optical element 216 may or may not have optical power, such as a static optical power.

Gaps between the optical elements 212-216 may be filled with the liquid crystal material 244 in at least the optic region 202 and the reservoir region 204. For example, gaps 218, 220, 222 and 224 may be filled with the liquid crystal material 244. The liquid crystal material may, in combination with at least the optical element 314, provide a dynamic optic to the ophthalmic device 200 by changing an orientation of the liquid crystals within the liquid crystal material 244.

The optic region 202 may be an optically active region of the ophthalmic device 200 and may include liquid crystal material 244 disposed between the optical elements 212-216 within gaps 218 and 220. The gap 218 being a space between optical elements 212 and 214 that may be filled with the liquid crystal material 244, and the gap 220 being a space between optical elements 214 and 216 that may also be filled with the liquid crystal material. The optic region 202 may be circular shaped and may be centered on an optical axis of the optical stack 246. The optic region 202, in some embodiments, may provide a dynamic optic to a user that provides accommodation by changing an orientation of the liquid crystal material, for example.

The reservoir region 204 may be a region that holds excess liquid crystal material. The reservoir region 204 may be formed by the gaps between adjacent ones of the optical elements 212-216 that are radially outside of the optic region 202. For example, the reservoir region 204 may be formed by the portion of the gap 222 that is between the optic region 202 and the dam 206. The portion of the gap 224 that is similarly situated would also form a part of the reservoir region 204. In general, the reservoir region 204 may begin on or before the separation and alignment features 242 are located, and the change between the optic region 202 and the reservoir region 204 may be gradual. In general, the reservoir region 204 may be radially outside of and may encircle the optic region 202. As such, the reservoir region 204 may be annular-shaped and disposed on a perimeter of the optical stack 246.

The dam 206 may be an area where the optical elements 212-216 contact or interlock, and may be formed to prevent the liquid crystal material 244 from leaking out of the reservoir region 204 and ultimately the optic region 202. The dam 206 may be formed by flat surfaces, e.g., sidewalls, of some of the grooves and ridges that form the alignment and separation features 242. The dam 206 may be arranged radially outward from and may encircle the reservoir region 204. In general, the dam 208 may be circumferential around a perimeter of the optical stack 246.

The seal region 208 may be a region for including a sealant, for example, to seal in the liquid crystal material 244. The seal region 208 may be formed by gaps between adjacent ones of the optical elements 212-216, such as gaps 226 and 228. In some embodiments, the seal region 208 may extend to an edge of the optical elements 212-216. The seal region 208 may also be annular-shaped and encircle the dam 206.

The alignment and separation features 242 associated with each optical element may, when the optical elements are formed into the optical stack 246, assist with radial alignment of the optical elements 212-216, and may cause the gaps 218-228 to be formed. The alignment and separation features 242 may additionally define the optic region 202, reservoir region 204, dam 206, and seal region 208. More specifically, the relative lateral positioning and size of the alignment and separation features 242 associated with each of the optical elements 212-216 may assist with setting widths of the various gaps and assist with radial alignment of the optical elements 212-216 to obtain concentricity.

The structures that form the alignment and separation features 242 may be formed in or on the optical elements 212-216, and may include various angles in relation to at least one surface of the optical elements 212-216. For example, the ridge 320 may extend up at an angle from an anterior surface of the optical element 214. In some embodiments, the angle may be less than 50°. In some embodiments, the angle the ridges and grooves make with posterior and/or anterior surfaces of the optical elements may affect various other features of the optical stack 246, such as electrical coatings formed on such surfaces for example.

The dam 206 may be formed upon stacking of the optical elements 212-216. The dam 206 may be formed in areas of the separation and alignment features 242 make contact. For example, the dam 206 may be formed where flat sidewalls of the ridges 228 and 236 rest of flat sidewalls of corresponding grooves 232 and 240. The resting of the optical elements 212-216 at those locations may provide intimate contact between adjacent ones of the optical elements 212-216. Additionally, the ridges and grooves that form the dam 208 may be offset from one another so that the ridges and grooves do not completely nest into one another. The amount of offset in combination with the heights/depths of the ridges and grooves may determine the widths of the various gaps 218-228. For example, the contact between optical elements 212 and 214 that occurs between ridge 228 and groove 232 may determine the width of gaps 218, 222, and 226. The contact point between ridge 228 and groove 232 may be affected by their relative amount of offset and their relative height/depth. For example, the ridges and grooves of the optical elements 212-216 may be around 30 to 90 microns in height/depth. It should also be noted that the width of gap 226, which may be larger than gaps 218 and 222, may also be formed by a change in thickness of the optical elements 212-216 in the seal region 208.

The widths of the gaps 218 and 220 in the optic region 202 may be determined by the dam 208, and may also be affected by the diffraction lens formed on the optical element 214. For example, the width of gaps 218 and 220 may be from 6 to 14 microns when including the diffraction lens aspect. If the diffraction lens aspect is ignored, the width of gaps 218 and 220 may be 2 to 10 microns. The widths of gaps 222 and 224 that form the reservoir region 204 may, for example, be 4 to 20 microns, and the width of gaps 226 and 228 that form the seal region 208 may be from 20 to 100 microns. In some embodiments, the width of gaps 222 and 224 may be, for example, 8 to 12 microns.

Radial alignment of the optical elements 212-216 may be assisted by the nesting of the grooves and ridges in the reservoir region 204, and further assisted by the width of the gap in the reservoir region 204. The grooves 226 and 232 and the ridges 230 and 238 may provide guides for aligning the optical axis of the optical elements 212-216, which may be nested as shown to provide coarse alignment. Additionally, the gap widths of the reservoir area may induce capillary forces to wick in excess liquid crystal material 244 from the optic region 202, for example. The capillary forces may further cause the gap widths on both sides of the nested grooves/ridges to equilibrate, which may provide more fine radial alignment of the optical elements 212-216.

The seal region 208 may have gap widths that provide space for inclusion of sealant material 248, such as a gasket or adhesive. For example, a liquid sealant material may wick into the gaps 226 and 228. In some embodiments, the liquid sealant material may be a curable adhesive that may be flash cured after wicking.

The optical stack 246 may be formed through various assembly steps. For example, a controlled volume of liquid crystal material 244 may be dispensed in the anterior side of the optical element 212, followed by the placement of the optical element 214 onto the volume of the liquid crystal material 244. The alignment and separations features 242 of the optical elements 212 and 214 may form the gap 218 and 222, and further radially align the two optical elements. Liquid crystal material 244 that may be in excess of a volume of the optic region 202 may be pulled into the reservoir region due to capillary forces. The capillary forces may cause the liquid crystal material 244 to equilibrate around the features in the reservoir region 204, which may provide finer alignment between the optical elements. A sealant material 248 may then be wicked into the seal region 208 between the optical elements 212 and 214. The sealant material 248 may then be treated to cause it to remain within the seal region 208.

The above steps may be performed again to add the optical element 216 to the optical stack 246. Alternatively, the three optical elements 212-216 may be assembled with the liquid crystal material 244 before sealant material 248 is applied and treated.

Figure 3:
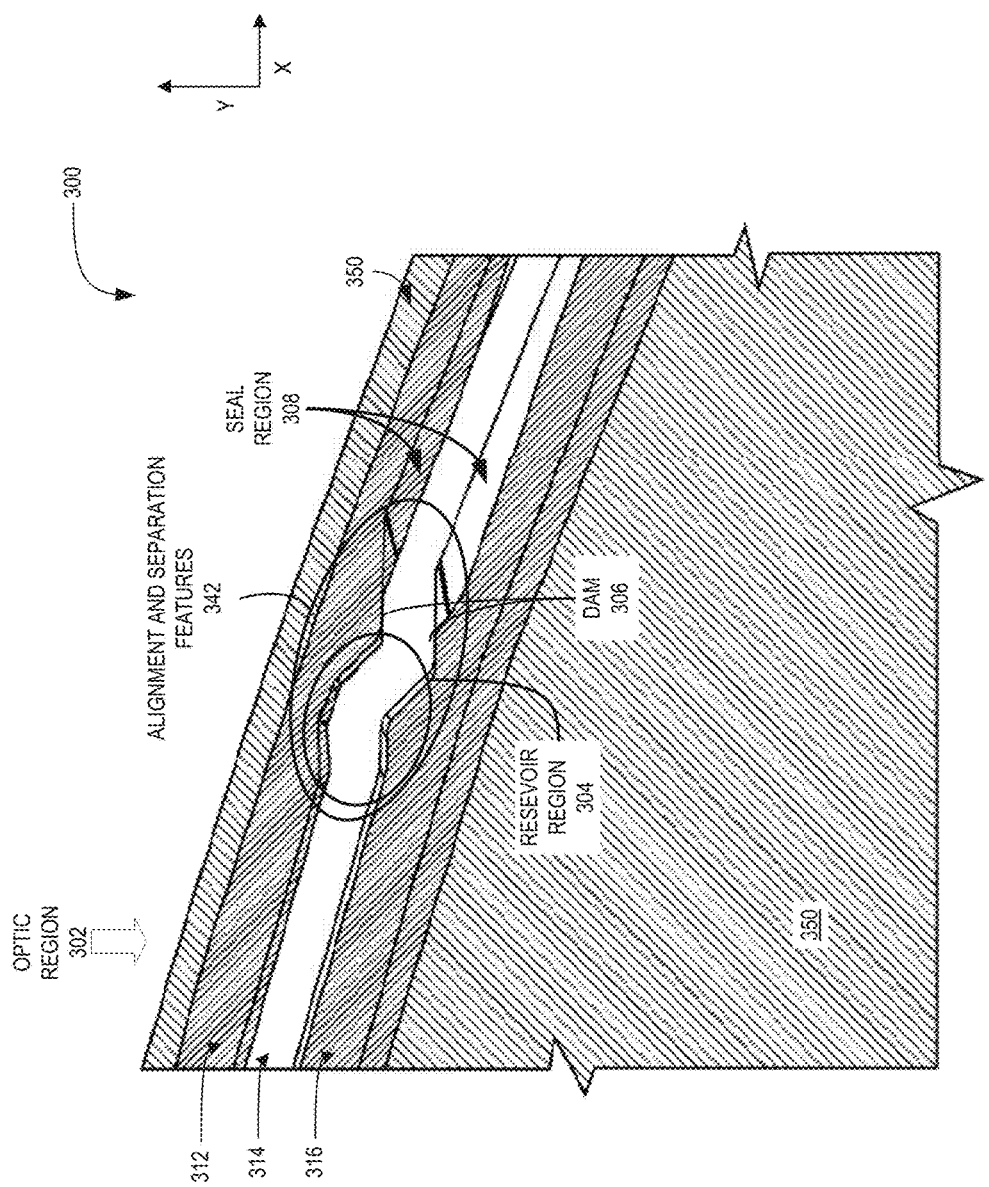
FIG. 3 is an illustrative cross-sectional view of a portion of an ophthalmic device 300 including alignment and separation features in accordance with an embodiment of the disclosure.

FIG. 3 is an illustrative cross-sectional view of a portion of an ophthalmic device 300 including alignment and separation features in accordance with an embodiment of the present disclosure. The ophthalmic device 300 may be an example of the ophthalmic device 100. The ophthalmic device 300 may include same or similar features as the ophthalmic device 200, for example, which may not be fully discussed in detail for sake of brevity. The illustrated embodiment of the ophthalmic device 300 includes optical elements 312, 314, and 316 that have separation and alignment features 342 formed therein and/or thereon. The separation and alignment features 342 may define an optic region 302, a reservoir region 304, a dam 306, and a seal region 308. The ophthalmic device 300 may be worn on an eye or implanted into an eye to provide accommodation, for example.

The optical elements 312-316 may form an optical stack, such as the optical stack 246, and which may be encased in enclosure 350. Enclosure 350 may provide a protective enclosure to the optical elements 312-316, including various other components of the ophthalmic device 300. Additionally, the enclosure 350 may be formed from a biocompatible material amenable to be worn on an eye or implanted into an eye. For example, encasement 350 may be fabricated of a common material (e.g., PolyMethylMethAcrylate or PMMA) or other optically transmissive materials.

Additionally, enclosure 350 may have a size and shape that mounts over the cornea of an eye. In the illustrated embodiment, enclosure 350 includes an external side, e.g., posterior side, having a convex shape and an eye-ward side, e.g., anterior side, having a concave shape. Of course, ophthalmic device 300 may assume other shapes and geometries including a piggyback configuration that attaches to a surface of an eye-mountable carrier substrate having an overall shape that resembles a conventional contact lens.

Optical element 312 may be hemispherical-shaped and may provide a top substrate of the optical stack. Further, the optical element 312 may be disposed between optical element 314 and enclosure 350. The optical element 312 may include a groove and a ridge to form associated alignment and separation features. For example, a shallow u-shaped groove may extend into the optical element 312 and a v-shaped ridge may extend out of the optical element 312. The optical element 312 may be formed from optically transmissive material, such as a transparent polymer. In some embodiments, the optical element 312 may be formed from a rigid, gas permeable polymer. Additionally, optical element 312 may provide optical power to the ophthalmic device 300 in some embodiments, and, in other embodiments, may not provide any optical power.

Optical element 314 may also be hemispherical-shaped and may include a diffraction lens on one or two surfaces within an optic region 302. For example, a diffraction lens may be formed on an external facing side (in the +Y direction) and/or on an eye-ward side (in the −Y direction). The optical element 314 may include grooves and ridges on both sides, such as the external facing side and the eye-ward side, that form associated alignment and separation features 342. For example, the optical element 314 has an upward bend followed by a downward bend that together form a serpentine-like shape in the optical element 314. The serpentine-like shape may form the alignment and separation features associated with the optical element 314. The serpentine-like shape in the optical element 314 may form grooves and ridges on both sides of the optical element 314. The optical element 314 may be formed from similar materials as the optical element 312 is formed.

Optical element 316 may also be hemispherical-shaped and may provide a bottom substrate of the optical stack. Further, the optical element 316 may be disposed between optical element 314 and enclosure 350 on the eye-ward side of the ophthalmic device 300. The optical element 316 may include a groove and a ridge to form associated alignment and separation features 342. For example, a shallow v-shaped ridge may extend up from the optical element 316, which is adjacent to a v-shaped ridge that also extends out of the optical element 316. In between the two v-shaped ridges a groove may be formed. The optical element 316 may be formed from similar materials as the other two optical elements are formed. Additionally, optical element 312 may provide optical power to the ophthalmic device 300 in some embodiments, and, in other embodiments, may not provide any optical power.

The separation and alignment features 342 include the ridges and grooves formed on or in each of the three optical elements. The relative location and interaction between the separation and alignment features 342 of each of the three optical elements may result in the formation of the various regions of the ophthalmic device 300, such as the optic region 302, reservoir region 304, dam 306, and seal region 308. For example, the flat areas of the grooves and ridges that make contact to form the dam 306 may also determine gap widths of the optic region 302 and the reservoir region 304. While a gap width of the seal region 308 may be additionally influenced by the dam 306, one or more of the optical elements 312-316 may become thinner in the seal region 308, which may also determine the gap width of the seal region 308.

The optic region 302 may be the optically active area of the ophthalmic device 300 and may be located over the cornea of a user's eye. The optic region 302 may include gaps between the optical elements that are filled with a liquid crystal material, for example. The liquid crystal material may be electrically stimulated to change orientations so that a change in optical power is provided by the ophthalmic device 300. The gaps may have a width of 2 to 10 microns, which may be determined by the alignment and separation features 342 of the optical elements 312-316 that form the dam 306.

The reservoir region 304 may be formed from the gaps between the adjacent optical elements that are between the optic region 302 and the dam 306. The gaps between the optical elements in the reservoir region 304 may have widths that are similar to, larger than, or smaller than the gap widths between the optical elements in the optic region 302. For example, the gap widths in the reservoir region 304 may be 4 to 20 microns.

The features of the optical elements that occur in the reservoir region 304 provide radial alignment between the optical elements so that concentricity of optical axes of the optical elements may be achieved. Nesting of the grooves and ridges that occur in the reservoir region may provide the radial alignment. Additionally, the gap widths in the reservoir region 304 may be on an order that capillary forces are induced in the reservoir region by the interaction of the optical elements and the liquid crystal material. The capillary forces may cause the gap width on both sides of the nested grooves/ridges may equilibrate that may cause concentricity to be achieved. Additionally, the capillary forces may assist with assembly of the ophthalmic device 100 by causing the optical elements to self-align.

The features of the optical elements that form the dam 306 may be laterally offset from mirror-like features on the adjacent optical elements. Offsetting the ridges/grooves that form the dam 306 may cause a flat surface, e.g., sidewall, of the ridges/grooves to contact one another. For example, the ridge extending down from the optical element 312 may be offset from the opposing groove of the optical element 314 so that the dam 306 is formed where sidewalls of those two features contact. The amount of offset and a height/depth of the ridges/grooves may set the gap widths in at least the optic region 302 and the reservoir region 304.

The seal region 308 may be formed radially outward of the dam 306, and may have gap widths that are larger than the gap widths of the optic region 302 and the reservoir region 304. For example, the gap widths that form the seal region 308 may be 30 to 100 microns. While the gap widths of the seal region 308 may be larger than the other discussed gap widths, the gap widths of the seal region may be small enough to induce wicking of a liquid sealant material into the seal region 308.

The various regions and the associated gaps may assist in the relative positioning of the optical elements 312-316 during assembly of the optical stack. For example, alignment and separation features 342 may assist with radial alignment of the optical elements 312-316 to obtain concentricity, and the dam 306 and the seal region 308 may reduce or eliminate the leakage of liquid crystal material out of the optic and reservoir regions 302, 304, respectively.

Figure 4:
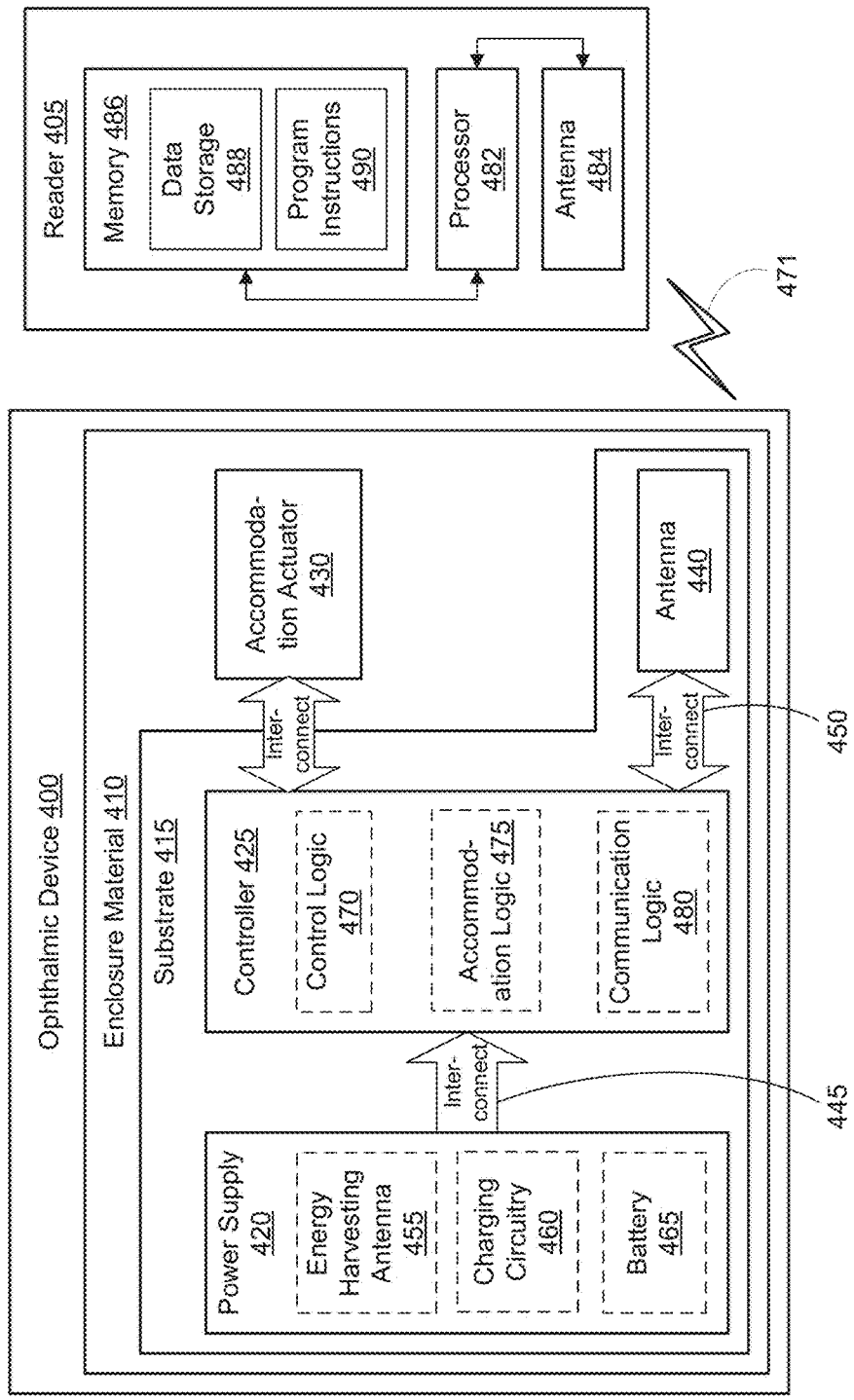
FIG. 4 is a functional block diagram of an ophthalmic device including alignment and separation features in accordance with an embodiment of the present disclosure

FIG. 4 is a functional block diagram of an ophthalmic device 400 including alignment and separation features in accordance with an embodiment of the present disclosure. Ophthalmic device 400 may be an on-eye device, such as a contact lens or a smart contact lens, or an implantable device, such as an intraocular lens. In the depicted embodiment, ophthalmic device 400 includes an enclosure material 410 formed to be either contact-mounted to a corneal surface of an eye or implanted into an eye. A substrate 415 is embedded within or surrounded by enclosure material 410 to provide a mounting surface for a power supply 420, a controller 425, an antenna 440, and various interconnects 445 and 450. The substrate 415 and the associated electronics may be one implementation of the control electronics 152. The illustrated embodiment of power supply 420 includes an energy harvesting antenna 455, charging circuitry 460, and a battery 465. The illustrated embodiment of controller 425 includes control logic 470, accommodation logic 475, and communication logic 480. As shown, accommodation actuator 430 is disposed in the enclosure material 410.

Power supply 420 supplies operating voltages to the controller 425 and/or the accommodation actuator 430. Antenna 440 is operated by the controller 425 to communicate information to and/or from ophthalmic device 400. In the illustrated embodiment, antenna 440, controller 425, and power supply 420 are disposed on/in substrate 415, while accommodation actuator 430 is disposed in enclosure material 410 (not in/on substrate 415). However, in other embodiments, the various pieces of circuitry and devices contained in ophthalmic device 400 may be disposed in/on substrate 415 or in enclosure material 410, depending on the specific design of ophthalmic device 400. For example, in one embodiment, accommodation actuator 430 may be disposed on a transparent substrate.

Substrate 415 includes one or more surfaces suitable for mounting controller 425, power supply 420, and antenna 440. Substrate 415 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 415 to form circuitry, electrodes, etc. For example, antenna 440 can be formed by depositing a pattern of gold or another conductive material on substrate 415. Similarly, interconnects 445 and 450 can be formed by depositing suitable patterns of conductive materials on substrate 415. A combination of resists, masks, and deposition techniques can be employed to pattern materials on substrate 415. Substrate 415 can be a relatively rigid material, such as polyethylene terephthalate ("PET") or another material sufficient to structurally support the circuitry and/or electronics within enclosure material 410. Ophthalmic device 400 can alternatively be arranged with a group of unconnected substrates rather than a single substrate 415. For example, controller 425 and power supply 420 can be mounted to one substrate 415, while antenna 440 is mounted to another substrate 415 and the two can be electrically connected via interconnects. Substrate 415 may also be a continuous piece of semiconductor, housing all or some of the aforementioned pieces of device architecture as integrated circuitry.

Substrate 415 can be shaped as a flattened ring with a radial width dimension sufficient to provide a mounting platform for the embedded electronic components. Substrate 415 can have a thickness sufficiently small to allow substrate f15 to be embedded in enclosure material fill without adversely influencing the profile of ophthalmic device 400. Substrate 415 can have a thickness sufficiently large to provide structural stability suitable for supporting the electronics mounted thereon. For example, substrate 415 can be shaped as a ring with a diameter of about 10 millimeters, a radial width of about 1 millimeter (e.g., an outer radius 1 millimeter larger than an inner radius), and a thickness of about 50 micrometers. Substrate 415 can optionally be aligned with the curvature of the eye-mounting surface of ophthalmic device 400 (e.g., convex surface). For example, substrate 415 can be shaped along the surface of an imaginary cone between two circular segments that define an inner radius and an outer radius. In such an example, the surface of substrate 415 along the surface of the imaginary cone defines an inclined surface that is approximately aligned with the curvature of the eye mounting surface at that radius.

In the illustrated embodiment, power supply 420 includes a battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with reader 405. Additionally or alternatively, power supply 420 may include a solar cell ("photovoltaic cell") to capture energy from incoming ultraviolet, visible, and/or infrared radiation. Furthermore, an inertial power scavenging system can be included to capture energy from ambient vibrations.

Charging circuitry 460 may include a rectifier/regulator to condition the captured energy for charging battery 465 or directly power controller 425 without battery 465. Charging circuitry 460 may also include one or more energy storage devices to mitigate high frequency variations in energy harvesting antenna 455. For example, one or more energy storage devices (e.g., a capacitor, an inductor, etc.) can be connected to function as a low-pass filter.

Controller 425 contains logic to choreograph the operation of the other embedded components. Control logic 470 controls the general operation of ophthalmic device 400, including providing a logical user interface, power control functionality, etc. Accommodation logic 475 includes logic for receiving signals from sensors monitoring the orientation of the eye, determining the current gaze direction or focal distance of the user, and manipulating accommodation actuator 430 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 480 provides communication protocols for wireless communication with reader 405 via antenna 440. In one embodiment, communication logic 480 provides backscatter communication via antenna 440 when in the presence of an electromagnetic field 471 output from reader 405. In one embodiment, communication logic 480 operates as a smart wireless radio-frequency identification ("RFID") tag that modulates the impedance of antenna 440 for backscatter wireless communications. The various logic modules of controller 425 may be implemented in software/firmware executed on a general purpose microprocessor, in hardware (e.g., application specific integrated circuit), or a combination of both.

Ophthalmic device 400 may include various other embedded electronics and logic modules. For example, a light source or pixel array may be included to provide visible feedback to the user. An accelerometer or gyroscope may be included to provide positional, rotational, directional or acceleration feedback information to controller 425.

The illustrated embodiment also includes reader 405 with a processor 482, an antenna 484, and memory 486. Memory 486 in reader 405 includes data storage 488 and program instructions 490. As shown reader 405 may be disposed outside of ophthalmic device 400, but may be placed in its proximity to charge ophthalmic device 400, send instructions to ophthalmic device 400, and/or extract data from ophthalmic device 400. In one embodiment, reader 405 may resemble a conventional contact lens holder that the user places ophthalmic device 400 in at night to charge, extract data, clean the lens, etc.

External reader 405 includes an antenna 484 (or group of more than one antennae) to send and receive wireless signals 471 to and from ophthalmic device 400. External reader 405 also includes a computing system with a processor 482 in communication with a memory 486. Memory 486 is a non-transitory computer-readable medium that can include, without limitation, magnetic disks, optical disks, organic memory, and/or any other volatile (e.g., RAM) or non-volatile (e.g., ROM) storage system readable by the processor 182. Memory 486 can include a data storage 488 to store indications of data, such as data logs (e.g., user logs), program settings (e.g., to adjust behavior of ophthalmic device 400 and/or external reader 405), etc. Memory 486 can also include program instructions 490 for execution by processor 482 to cause the external reader 405 to perform processes specified by the instructions 490. For example, program instructions 490 can cause external reader 405 to provide a user interface that allows for retrieving information communicated from ophthalmic device 400 or allows transmitting information to ophthalmic device 400 to program or otherwise select operational modes of ophthalmic device 400. External reader 105 can also include one or more hardware components for operating antenna 484 to send and receive wireless signals 471 to and from ophthalmic device 400.

External reader 405 can be a smart phone, digital assistant, or other portable computing device with wireless connectivity sufficient to provide the wireless communication link 471. External reader 405 can also be implemented as an antenna module that can be plugged into a portable computing device, such as in an embodiment where the communication link 471 operates at carrier frequencies not commonly employed in portable computing devices. In some instances, external reader 405 is a special-purpose device configured to be worn relatively near a wearer's eye to allow the wireless communication link 471 to operate with a low power budget. For example, the external reader 405 can be integrated in a piece of jewelry such as a necklace, earring, etc. or integrated in an article of clothing worn near the head, such as a hat, headband, etc.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device comprising:
   first, second, and third optical elements arranged in a stack, each optical element of the first, second, and third optical elements including alignment and separation features formed at a radius thereof, wherein the alignment and separation features of each optical element correspond to like features on at least one of the other optical elements, the alignment and separation features forming:
   a reservoir region to provide radial alignment to the first, second, and third optical elements such that an optical axis of each optical element is aligned, the reservoir region having a reservoir region gap formed between adjacent ones of the first, second, and third optical elements; and
   a dam region, disposed radially outside of the reservoir region, including a first dam formed due to the first and second optical elements being in contact, and a second dam formed due to the second and third optical elements being in contact, wherein the dam region determines a reservoir region gap width of each reservoir region gap.

2. The ophthalmic device of claim 1, wherein the alignment and separation features further form an optic region encircled by the reservoir region, the optic region centered on the optical axis of each of the optical elements, wherein the optic region has an optic region gap formed between adjacent ones of the first, second, and third optical elements, and wherein the dam region determines an optic region gap width of each optic region gap.

3. The ophthalmic device of claim 2, wherein the optic region gap width and the reservoir region gap width are different widths.

4. The ophthalmic device of claim 2, wherein a liquid crystal material is disposed within the optic region gap and the reservoir region gap.

5. The ophthalmic device of claim 2, wherein the reservoir region is coupled to hold excess liquid crystal material from the optic region.

6. The ophthalmic device of claim 1, wherein the alignment and separation features further form a seal region, disposed radially outward of the dam region, the seal region having a seal region gap formed between adjacent ones of the first, second, and third optical elements, wherein the dam region determines a seal region gap width of each seal region gap.

7. The ophthalmic device of claim 1, wherein the dam region prevents liquid crystal material from escaping the reservoir area in a radially outward direction.

8. The ophthalmic device of claim 1, wherein the alignment and separation features are formed from grooves and ridges disposed on one or more surfaces of each of the first, second, and third optical elements.

9. The ophthalmic device of claim 8, wherein the grooves and ridges of the first optical element are formed on one surface of the first optical element, the one surface of the first optical element facing the second optical element.

10. The ophthalmic device of claim 8, wherein the grooves and ridges of the third optical element are formed on one surface of the third optical element, the one surface of the third optical element facing the second optical element.

11. The ophthalmic device of claim 8, wherein the grooves and ridges of the second optical element are formed on two surfaces of the second optical element, wherein one of the two surfaces faces the first optical element, and the other of the two surfaces faces the third optical element.

12. An apparatus, comprising:
first, second, and third optical elements arranged in a stack, wherein each of the first, second, and third optical elements includes alignment and separation features corresponding to like features on at least one of the other first, second, and third optical elements,
wherein the alignment and separation features provide radial alignment between the first, second, and third optical elements,
wherein adjacent ones of the first, second, and third optical elements are coupled at a sidewall of the alignment and separation features to form a dam, and
wherein each of an optic region, a reservoir region, and a seal region are formed by a respective gap between adjacent ones of the first, second, and third optical elements, and
wherein a width of the respective gaps formed between adjacent ones of the first, second, and third optical elements is determined by the sidewall of the alignment and separation features that couple to form the dam.

13. The apparatus of claim 12, wherein the alignment and separation features included in each of the first, second, and third optical elements are annular-shaped and formed around a perimeter of the first, second, and third optical elements, and wherein the alignment and separation features define the optic region, the reservoir region, and the seal region.

14. The apparatus of claim 12, wherein the alignment and separation features included in each of the first, second, and third optical elements include one or more ridges and one or more grooves arranged to at least partially align to mirror-like grooves and ridges on an adjacent one of the first, second, and third optical elements.

15. The apparatus of claim 14, wherein a ridge of the second optical element nests within a groove of the first optical element to provide the radial alignment between the first and second optical elements, and wherein a sidewall of a ridge of the first optical element rests on a sidewall of a groove of the second optical element to form the dam between the first and second optical elements.

16. The apparatus of claim 15, wherein the dam formed between the first and second optical elements determines the width of the optic region gap, the reservoir region gap, and the seal region gap formed between the first and second optical elements.

17. The apparatus of claim 14, wherein a ridge of the third optical element nests within a groove of the second optical element to provide the radial alignment between the second and third optical elements, and wherein a sidewall of a ridge of the second optical element rests on a sidewall of a groove of the third optical element to form the dam between the second and third optical elements.

18. The apparatus of claim 15, wherein the dam formed between the second and third optical elements determines the width of the optic region gap, the reservoir region gap, and the seal region gap formed between the second and third optical elements.

19. The apparatus of claim 12, further including a liquid crystal material disposed within the respective gaps forming the optic region, and reservoir region occurring between adjacent ones of the first, second, and third optical elements.

20. The apparatus of claim 12, wherein the seal region formed between adjacent ones of the first, second, and third optical elements is formed for the inclusion of a sealant material.

21. The apparatus of claim 20, wherein the dam prevents sealant material from breaching the reservoir region in a radially inward direction.

22. The apparatus of claim 12, wherein the respective gaps that form the optic, reservoir, and seal regions between adjacent ones of the first, second, and third optical elements have different gap widths.

23. The apparatus of claim 12, wherein a width of each gap that forms the reservoir region is from four to twenty microns.

24. The apparatus of claim 12, wherein a width of each gap that forms the seal region is from 20 to 100 microns.

25. The apparatus of claim 12, wherein the optic region includes a center diameter of the apparatus, wherein the reservoir region encircles the optic region, wherein the dam encircles the reservoir region, and wherein the seal region encircles the dam.

* * * * *